United States Patent [19]

Ryan

[11] Plant 4,363

[45] Jan. 2, 1979

[54] IMPATIENS PLANT

[76] Inventor: John J. Ryan, 39877 Sundale Dr., Fremont, Calif. 94538

[21] Appl. No.: 875,584

[22] Filed: Feb. 6, 1978

[51] Int. Cl.[2] ..... A01H 5/00
[52] U.S. Cl. ..... Plt./68
[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Apache, and discovered by me in commercial greenhouses in Fremont, Calif. Apache is closest in characteristics to Red Magic, but is particularly characterized by its thicker, richer dark foliage; no variegation; a small red flower that is slightly cupped; a more upright growth habit; and fewer flowers than Red Magic.

1 Drawing Figure

BACKGROUND OF THE INVENTION

The present new variety (seedling) was discovered by me in a commercial greenhouse in Fremont, Calif., as a result of the cross pollination of the unpatented pistil parent 75-4 and the unpatented pollen parent 75-7.

Asexual reproduction of my new cultivar by terminal or stem cuttings grown in pots in a plastic (polyethylene) greenhouse in Fremont, Calif., under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Apache is closest in characteristics to Red Magic. The following outstanding characteristics of Apache distinguish it from Red Magic:

1. Less flowers than Red Magic.
2. Flower color is darker and less of a rose-red.
3. Thicker, richer, darker foliage.
4. Flowers smaller and slightly cupped.
5. Growth habit is more upright.

DESCRIPTION OF THE PHOTOGRAPH

The accompanying colored photograph illustrates the overall appearance of the cultivar Apache, showing the colors as true as reasonably possible for this type of colored reproduction. The colors of the foliage and flower are so deep that environmental conditions have little effect on them.

DETAILED DESCRIPTION

The following detailed description of Apache was based on observations made of the new cultivar on Jan. 13, 1977.

I. Plant

Name: Apache.
Origin: Seedling of the cross pollination of unpatented pistil parent 75-4 and unpatented pollen parent 75-7.
Form. Upright.
Height to flowering: 45 cm.
Growth: Fast.
Type of cutting: Terminal or stem.

Rooting time: Typical, 10–14 days.
Rooting habit: Fast, dendritic.

II. Foliage

Arrangement: Lower leaves on any breaking are opposite (usually one set); whorls of 3 and 4 (some whorls of 6 and 7 due to compressed nodes).
Shape: Elliptical to oblanceolate.
Tip: Broadly acuminate.
Base: Attenuate.
Margin: Ciliate-secretion on end of hairs at base of leaf.
Venation: Pinnate.
Size: Blade and petiole 7.5 cm. to 14.0 cm.; length of blade 5.5 cm. to 10.5 cm.; width of blade at widest point 2.5 cm. to 4.5 cm.
Surface: Glabrous and waxy.
Variegation: None.
Color: Dark red-brown.

1. *Petiole* } Upper 185 B, lower 185 A
2. *Veins* }
3. *Leaf.*—a. Upper 187 A. b. Lower 53 A.

III. Stem

Color: 46 A.
Internode:

1. *Length.*—Moderate.
2. *Size.*—Moderate.

Node expanded: (relative to internode) Little, if any.
Breaking action: Moderate.

IV. Flower

Form: Typical, but slightly cupped.
Borne: End of branches, terminal.
Blooming habit:

1. *Relative number.*—Moderate, depending heavily on cultural conditions.
2. *Time to flowering.*—Moderate to long.
3. *Longevity.*—3–5 days, typical.

Size of mature flower: First flower on a plant may be small.

1. *Length.*—4.5 cm. to 6.0 cm.
2. *Width.*—4.5 cm. to 6.0 cm.
3. *Spur.*—5.5 cm. to 6.5 cm.

Color: Little color change under high heat and light.

1. *Eye.*—46 C.
2. *Middle* } 43 A
3. *Edge* }
4. *Pedicel.*—46 D.

V. Reproductive Organs

Stamens:

1. *Anthers* } Typical, fused hood over pistil
2. *Filaments* }
3. *Pollen.*—a. Color: 155B. b. Abundance: Typical, plenty.

Pistils:

1. *Style* } Typical
2. *Ovaries* }

VI. Other Characteristics

Insects: Apache has less mite problems than most other varieties.

I claim:

1. A new and distinct form of Impatiens plant as described and illustrated, known by the cultivar name Apache, and particularly characterized by a thick, rich, dark foliage; no variegation; a deep red flower that is slightly cupped; and a very upright growth habit.

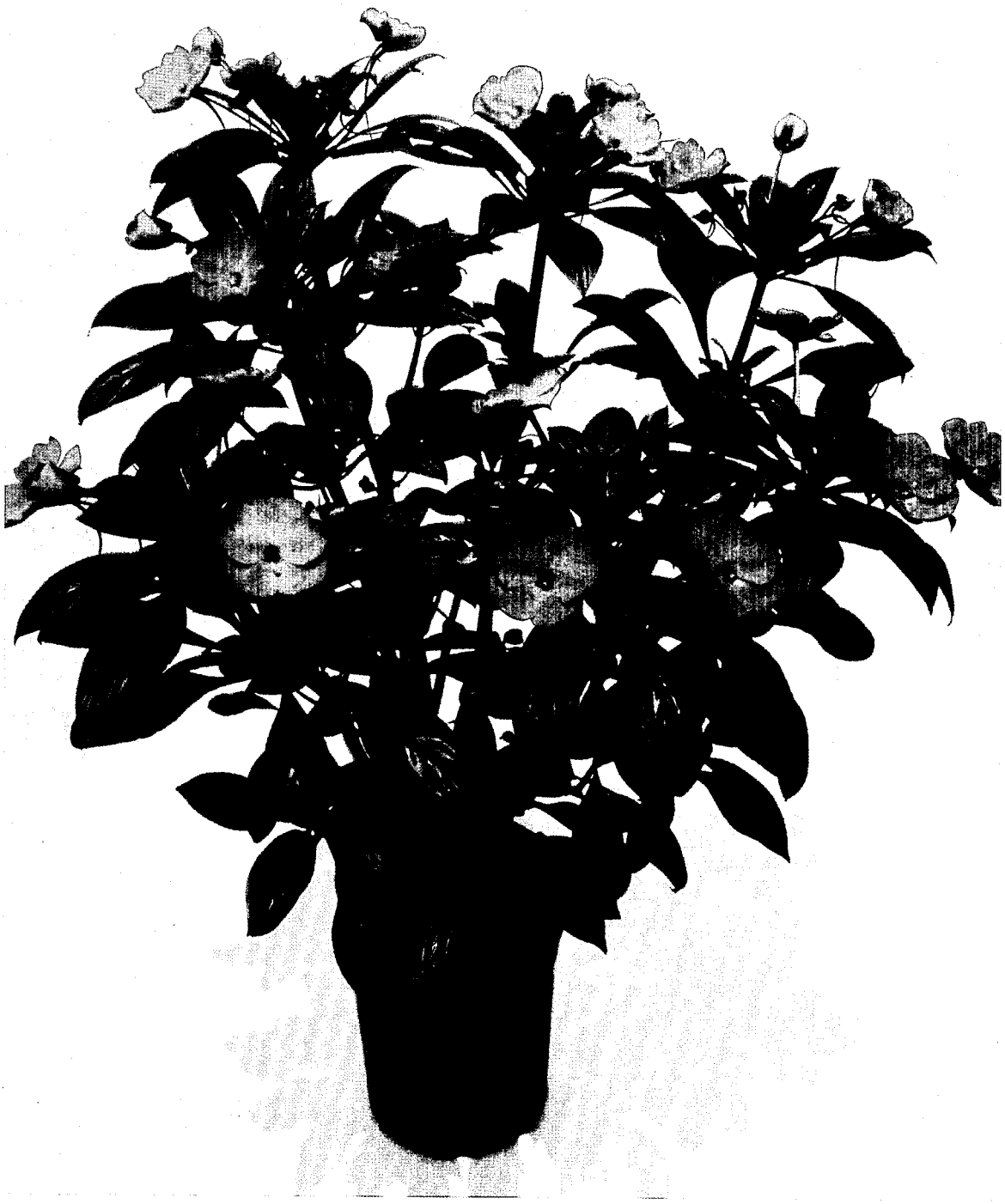

* * * * *